United States Patent
Isoda et al.

(10) Patent No.: US 10,746,740 B2
(45) Date of Patent: *Aug. 18, 2020

(54) BIOLOGICAL SUBSTANCE QUANTITATION METHOD, PATHOLOGICAL DIAGNOSIS SUPPORT SYSTEM, AND RECORDING MEDIUM STORING COMPUTER READABLE PROGRAM

(71) Applicant: KONICA MINOLTA, INC., Chiyoda-ku (JP)

(72) Inventors: Takeshi Isoda, Sayama (JP); Naoko Furusawa, Hino (JP); Yasuyuki Motokui, Kunitachi (JP); Kohsuke Gonda, Sendai (JP); Noriaki Ohuchi, Sendai-chi (JP); Mika Watanabe, Sendai (JP)

(73) Assignee: Konica Minolta, Inc., Tokyo (JP)

( * ) Notice: Subject to any disclaimer, the term of this patent is extended or adjusted under 35 U.S.C. 154(b) by 144 days.

This patent is subject to a terminal disclaimer.

(21) Appl. No.: 15/544,795

(22) PCT Filed: Jan. 15, 2016

(86) PCT No.: PCT/JP2016/051116
§ 371 (c)(1),
(2) Date: Jul. 19, 2017

(87) PCT Pub. No.: WO2016/117466
PCT Pub. Date: Jul. 28, 2016

(65) Prior Publication Data
US 2018/0275134 A1 Sep. 27, 2018

(30) Foreign Application Priority Data

Jan. 22, 2015 (JP) .................... 2015-009938

(51) Int. Cl.
| | |
|---|---|
| *G01N 33/536* | (2006.01) |
| *G01N 33/48* | (2006.01) |
| *G01N 33/58* | (2006.01) |
| *G01N 33/68* | (2006.01) |

(52) U.S. Cl.
CPC .......... *G01N 33/582* (2013.01); *G01N 33/48* (2013.01); *G01N 33/536* (2013.01); *G01N 33/587* (2013.01); *G01N 33/6875* (2013.01)

(58) Field of Classification Search
CPC .... G01N 33/582; G01N 33/48; G01N 33/536; G01N 33/587; G01N 33/6895
See application file for complete search history.

(56) References Cited

U.S. PATENT DOCUMENTS

| | | | | | |
|---|---|---|---|---|---|
| 9,189,678 | B2* | 11/2015 | Tsunomori | ........... | G06T 7/0012 |
| 9,483,684 | B2* | 11/2016 | Tsunomori | ......... | G01N 21/6456 |
| 9,972,087 | B2* | 5/2018 | Isoda | ......... | G06T 7/90 |
| 10,175,220 | B2* | 1/2019 | Watanabe | .......... | G01N 33/4833 |
| 2003/0157523 | A1 | 8/2003 | Frantz et al. | | |
| 2009/0086314 | A1* | 4/2009 | Namba | .............. | G01N 21/6458 359/383 |
| 2013/0157895 | A1* | 6/2013 | Aimiya | .................... | G01N 1/30 506/9 |
| 2019/0113497 | A1* | 4/2019 | Watanabe | .......... | G01N 33/4833 |

FOREIGN PATENT DOCUMENTS

| | | |
|---|---|---|
| EP | 2613138 | 7/2013 |
| JP | 2005-509870 | 4/2005 |
| JP | 2007-513334 | 5/2007 |
| JP | 2008-514209 | 5/2008 |
| JP | 2009-509171 | 3/2009 |
| JP | 2009-527740 | 7/2009 |
| JP | 2011-209220 | 10/2011 |
| JP | 2012-208106 | 10/2012 |
| JP | 2013-088296 | 5/2013 |
| WO | WO 2007/095644 | 8/2007 |
| WO | WO 2012/029752 | 3/2012 |
| WO | WO 2013/146694 | 10/2013 |
| WO | WO 2013/146741 | 10/2013 |
| WO | WO 2013/146841 | 10/2013 |
| WO | WO 2013/146843 | 10/2013 |
| WO | WO 2015/045962 | 4/2015 |

OTHER PUBLICATIONS

Search Report dated Oct. 23, 2017 which issued in the corresponding European Patent Application No. 16740073.8.

Gonda et al. "Development of a Quantitative Diagnostic Method of Estrogen Receptor Expression Levels by Immunohistochemistry using Organic Fluorescent Material-Assembled Nanoparticles", Biochemical and Biophysical Research Communications, vol. 426, No. 3, Aug. 29, 2012, pp. 409-414.

H. Goda et al., "Development of a Quantitative Diagnostic Method of Estrogen Receptor Expression Levels by Immunohistochemistry using Fluorescent Nanoparticles", Konica Minolta Technology Report, 2014, vol. 11, pp. 68-72.

V. Tuominen et al., "ImmunoRatio-F: image analysis of Ki-67 using cytokeratin immunofluorescence correction", 11th European Congress on Telepathology and 5th International Congress on Virtual Microscopy, Jun. 8, 2012.

(Continued)

*Primary Examiner* — Gailene Gabel
(74) *Attorney, Agent, or Firm* — Cozen O'Connor

(57) ABSTRACT

There is provided a biological substance quantitation method of quantitating a biological substance in a sample stained with a staining reagent including a fluorescent particle encapsulating a fluorescent substance, based on a fluorescence of the fluorescent substance. The method includes inputting a fluorescent image representing expression of the biological substance in the sample by a fluorescent bright spot; and quantitating an expression amount of the biological substance based on a fluorescence of the fluorescent bright spot. The biological substance is a nucleoprotein expressed at a cell nucleus. The fluorescent particle binds to the biological substance through a primary antibody which is directed against the biological substance as an antigen.

3 Claims, 6 Drawing Sheets

(56) References Cited

OTHER PUBLICATIONS

International Preliminary Report on Patentability and Written Opinion dated Jul. 26, 2017.
Office Action dated Aug. 6, 2019 issued in Japanese Patent Application No. 2016-570607.
Konica Minolta Inc., "Development of a Quantitative Diagnostic Method of Estrogen Receptor Expression Levels by Immunohistochemistry Using Fluorescent Nanoparticles", 2014, pp. 68-72, vol. 11.
Office Action dated Mar. 23, 2020 issued in Japanese Patent Application No. 2016-570607.

* cited by examiner

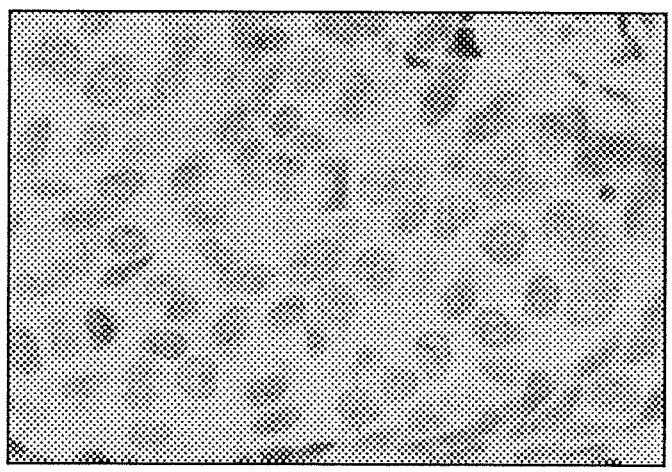
FIG. 7A
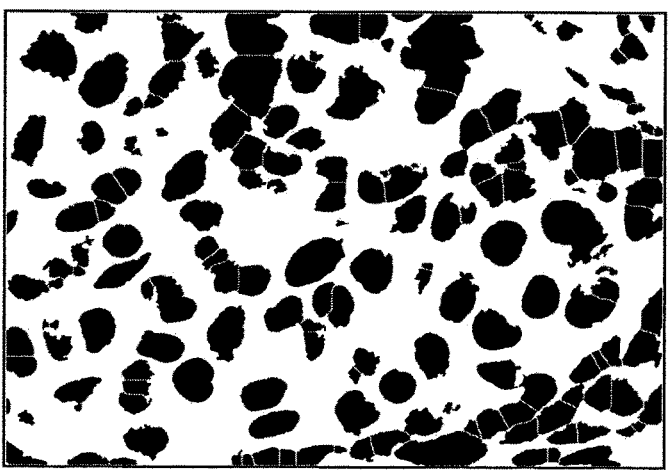
FIG. 7B
FIG. 8
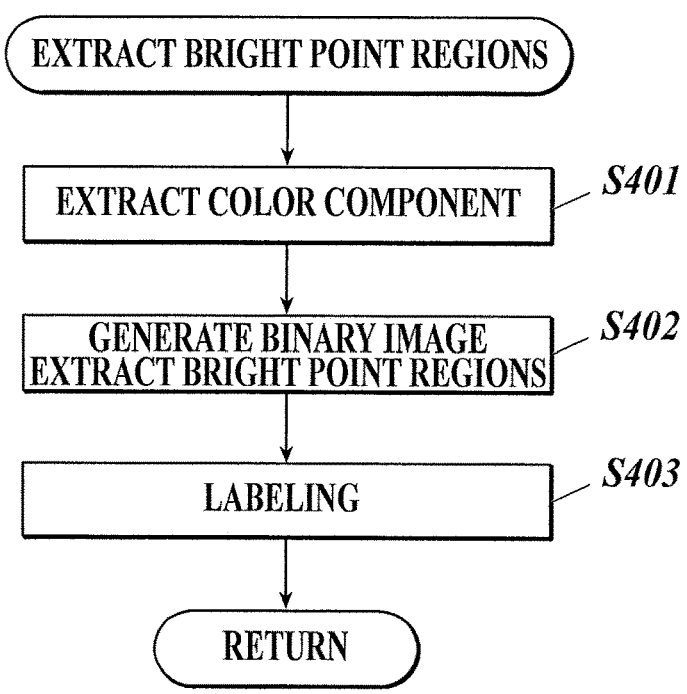

BIOLOGICAL SUBSTANCE QUANTITATION METHOD, PATHOLOGICAL DIAGNOSIS SUPPORT SYSTEM, AND RECORDING MEDIUM STORING COMPUTER READABLE PROGRAM

RELATED APPLICATIONS

This is a U.S. National Phase Application under 35 USC 371 of International Application PCT/JP2016/051116 filed on Jan. 15, 2016.

This application claims the priority of Japanese application no. 2015-009938 filed Jan. 22, 2015, the entire content of which is hereby incorporated by reference.

TECHNOLOGICAL FIELD

The present invention relates to a biological substance quantitation method, a pathological diagnosis support system, and a program using information of the luminance of a fluorescent substance.

BACKGROUND ART

In pathological diagnosis, specifying the kind and expression amount of protein overexpressing in a sample, such as tissue slice, is very important information for prognostic expectation and for determination of future treatment plan.

For example, the expression of Ki67 protein, which is a protein expressed in a cell nucleus during cell division, is evaluated in order to determine the proliferation and/or malignancy of various kinds of tumor.

According to the technique described in Patent Document 1, the risk of cancer relapse is determined from cells collected from a breast cancer patient, for example, on the basis of the number of cells in which Ki67 protein is expressed or the expression amount of Ki67 protein.

PRIOR ART DOCUMENT

Patent Document

Patent Document 1: Japanese Patent Application Laid-Open Publication No. 2011-209220

SUMMARY

Problems to be Solved by the Invention

In Patent Document 1, specifically, Ki67 protein is labelled by staining method using an enzyme as a dye (for example, DAB staining method). Such staining method makes it relatively easy to extract cells in which Ki67 protein is expressed by judging whether Ki67 protein is expressed or not, however, the expression amount is quantitated with a low accuracy and a low reproducibility. There is a problem that the expression level cannot be evaluated quantitatively.

A main object of the present invention is to provide a biological substance quantitation method, a pathological diagnosis support system, and a program for accurate quantitation of the expression amount of a nucleoprotein in a sample.

Means for Solving the Problem

In order to solve the above-mentioned problem, according to one aspect of the present invention, there is provided a biological substance quantitation method of quantitating a biological substance in a sample stained with a staining reagent including a fluorescent particle encapsulating a fluorescent substance, based on a fluorescence of the fluorescent substance, the method including:

inputting a fluorescent image representing expression of the biological substance in the sample by a fluorescent bright spot; and quantitating an expression amount of the biological substance based on a fluorescence of the fluorescent bright spot, wherein the biological substance is a nucleoprotein expressed at a cell nucleus, and the fluorescent particle binds to the biological substance through a primary antibody which is directed against the biological substance as an antigen.

According to another aspect of the biological substance quantitation method of the present invention, the primary antibody is a monoclonal antibody.

According to another aspect of the biological substance quantitation method of the present invention, the fluorescent particle binds to the biological substance through a secondary antibody which is directed against the primary antibody as an antigen, and the secondary antibody is a monoclonal antibody.

A polyclonal antibody includes a mixture of several kinds of antibody components and reacts with a plurality of epitopes on the antigen in immunostaining. Accordingly, it is known that expression of specific protein is detected with high sensitivity by immunostaining with a polyclonal antibody than by immunostaining with a monoclonal antibody. The present invention is different from the conventional technique in that expression of a biological substance can be detected with high sensitivity even by using a monoclonal antibody.

According to another aspect of the biological substance quantitation method of the present invention, the staining reagent is a mixed reagent of two or more kinds of reagents each including a fluorescent substance having an emission wavelength different from each other, the two or more kinds of reagents stain the biological substance of a single kind with the fluorescent substance having an emission wavelength different from each other, in the inputting, fluorescent images are input for each emission wavelength of the fluorescent substance and represent expression of the biological substance in the sample by a fluorescent bright spot based on a fluorescence of the fluorescent substance in the mixed reagent, and in the quantitating, the expression amount of the biological substance is quantitated based on a fluorescence of the fluorescent bright spot in the fluorescent images input for each emission wavelength of the fluorescent substance, the method further including summing the expression amount of the biological substance quantitated for each emission wavelength of the fluorescent substance.

When the quantitated biological substance is a nucleoprotein and expressed densely in cell nuclei, such as Ki67 protein, a plurality of fluorescent particles corresponding to a plurality of biological substances in proximity to each other are likely to be observed as one bright point, and results in low accuracy in quantitation. In such cases, by using two or more colors of fluorescent particles which can stain the same kind of biological substances, fluorescent particles can be separately observed even when they are disposed in proximity to each other with an interval smaller than the resolution of the microscope. This improves accuracy in quantitation of biological substances in the sample, even when the resolution of the microscope is relatively low.

Advantageous Effects of Invention

According to the present invention, the expression amount of a nucleoprotein in a sample can be quantitated with high accuracy.

BRIEF DESCRIPTION OF THE DRAWINGS

FIG. 7A is a diagram illustrating a bright field image;

FIG. 7B is a diagram illustrating an image of extracted cells;

FIG. 8 is a flowchart illustrating the detailed process in Step S4 of FIG. 5;

EMBODIMENT FOR CARRYING OUT THE INVENTION

Embodiments for carrying out the present invention will now be described with reference to the attached drawings, which should not be construed to limit the present invention.

<Configuration of Pathological Diagnosis Support System 100>

Figure 1:
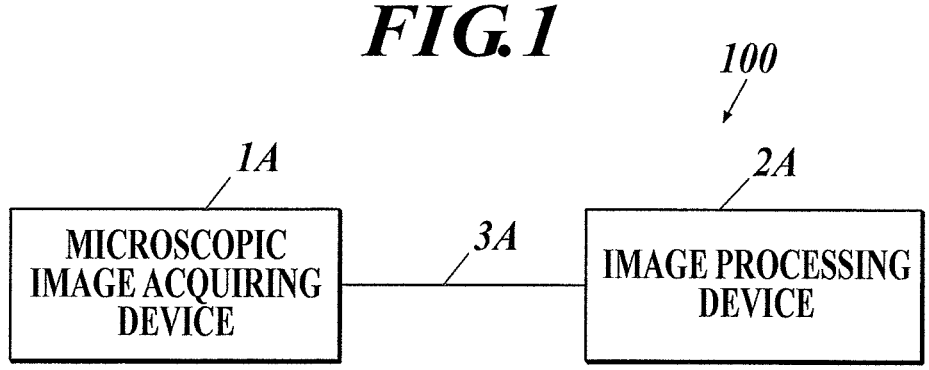
FIG. 1 is a diagram showing a configuration of a pathological diagnosis assistance system using the biological substance quantitation method according to the present invention.

FIG. 1 illustrates an exemplary overall configuration of a pathological diagnosis support system 100 that employs the quantitative determination method of a biological substance according to the present invention. The pathological diagnosis support system 100 acquires a microscopic image of a tissue sample stained with a predetermined staining reagent, analyzes the acquired microscopic image, and outputs a feature quantity which quantitatively represents expression of a specific biological substance in the tissue sample of observation target.

As illustrated in FIG. 1, the pathological diagnosis support system 100 includes a microscopic image acquiring device 1A, an image processing device 2A, and an interface, such as a cable 3A, connecting the microscopic image acquiring device 1A and the image processing device 2A for transmission and reception of data. The microscopic image acquiring device 1A may be connected to the image processing device 2A in any manner. For example, the microscopic image acquiring device 1A and the image processing device 2A may be connected through a local area network (LAN) or wireless communication.

Furthermore, the pathological diagnosis support system 100 may include a staining device which automatically stains the sample.

The microscopic image acquiring device 1A is a known optical microscope provided with a camera, which acquires a microscopic image of a tissue sample on a microscopic slide placed on a slide fixation stage, and transmits the microscopic image to the image processing device 2A.

The microscopic image acquiring device 1A includes an irradiator, a focusing unit, a photographing unit, and a communication interface (I/F). The irradiator includes a light source and a filter, and emits light toward the tissue sample on the microscopic slide placed on the slide fixation stage. The focusing unit includes an eyepiece lens and an object lens. The focusing unit focuses transmitted light, reflected light, or fluorescent light, which is emitted from the tissue sample on the microscopic slide in response to the irradiated light, into an image. The photographing unit includes a charge coupled device (CCD) sensor. The photographing unit is specifically a camera disposed in a microscope to photograph an image formed by the focusing unit, and produce the digital image data of the microscopic image. The communication interface transmits the image data of the microscopic image to the image processing device 2A. The microscopic image acquiring device 1A in the present embodiment includes a bright field unit suitable for bright field microscopy composed of a combination of an irradiating subunit and a focusing subunit, and a fluorescence unit suitable for fluorescent microscopy composed of a combination of an irradiating subunit and a focusing subunit, and can switch between these units, i.e., between bright field observation and fluorescence observation.

The microscopic image acquiring device 1A may be a super resolution microscopy which acquires an image using structured illumination (SIM: Structured Illumination Microscopy) described in WO2014/005195A, for example. According to the super resolution microscopy using structured illumination, the entire visual field is illuminated with two coherent beams to make a cross-stripe pattern of light on the sample. The resulting moire effect makes it possible to capture and analyze a diffraction light which has not been conventionally captured. High resolution microscopic images can be thus acquired. While the resolution (the minimum distance between two distinguishable adjacent points) by the conventional optical microscopy is about 200 nm due to the diffraction limit of light, the resolution realized by the super resolution microscopy using structured illumination is about 100 nm.

Besides the microscope provided with a camera, the microscopic image acquiring device 1A may be any device, for example, a virtual microscopic slide preparing device that scans a microscopic slide placed on a slide fixation stage of a microscope to acquire a microscopic image of an overall tissue sample (see Japanese Publication of International Patent Application No. 2002-514319, for example). The virtual microscopic slide preparing device can acquire image data of the overall tissue sample that can be displayed on a display at once.

The image processing device 2A analyzes the microscopic image transmitted from the microscopic image acquiring device 1A to calculate the distribution of the expression of the specific biological substance in the target tissue sample.

Figure 2:
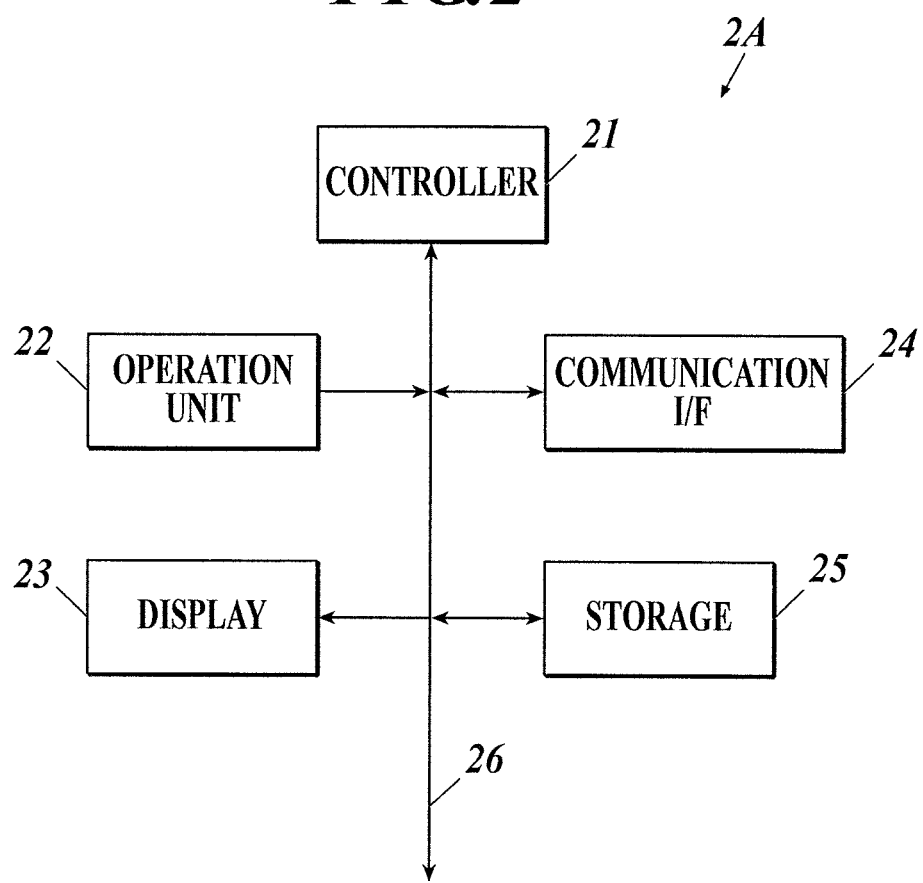
FIG. 2 is a block diagram showing a functional configuration of an image processing device in FIG. 1.

FIG. 2 illustrates an exemplary functional configuration of the image processing device 2A. As illustrated in FIG. 2, the image processing device 2A includes a controller 21, an operating unit 22, a display 23, a communication interface 24, and a storage 25, which are connected to each other through a bus 26.

The controller 21 includes a central processing unit (CPU), a random access memory (RAM), and the like. The controller 21 executes multiple processes in cooperation with a variety of programs stored in the storage 25 to control the overall operation of the image processing device 2A. For example, the controller 21 executes image analysis in cooperation with a program stored in the storage 25 (see FIG. 5) to and functions as a unit executing a quantitation step for quantitating the expression amount of the biological substance and a step for summing The operating unit 22 includes a keyboard including keys for inputting characters and numbers and several functional keys, and a pointing device, such as a mouse. The operating unit 22 outputs input signals to the controller 21, i.e., signals generated by press of keys on the keyboard and by operation of the mouse.

The display 23 includes a monitor, such as a cathode ray tube (CRT) display or a liquid crystal display (LCD). The display 23 displays a variety of windows in response to display signals input from the controller 21. The display 23 in the present embodiment functions as an output unit for outputting the results of image analysis.

The communication interface 24 allows data transmission and reception between the microscopic image acquiring device 1A and external devices, such as the microscopic image acquiring device 1A. The communication interface 24 functions as an input unit of inputting a bright field image and a fluorescent image.

The storage 25 includes a hard disk drive (HDD) or a nonvolatile memory composed of a semiconductor, for example. The storage 25 stores a variety of programs and data as described above.

Besides, the image processing device 2A may include a LAN adaptor and a router to be connected to external devices through a communication network, such as a LAN.

The image processing device 2A in the present embodiment preferably analyzes the sample using the bright field image and fluorescent image transmitted from the microscopic image acquiring device 1A.

Figure 3:
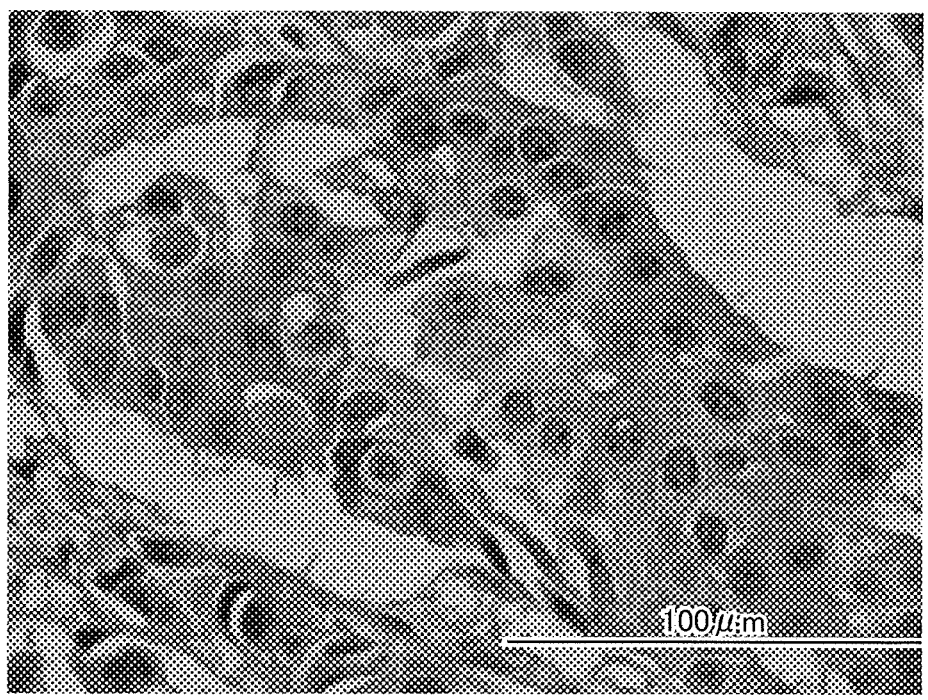
FIG. 3 is a diagram illustrating an exemplary bright field image.

The bright field image is a microscopic image of a tissue sample stained with a hematoxylin (H) staining reagent or a hematoxylin-eosin (HE) staining reagent focused and photographed in the bright field with the microscopic image acquiring device 1A. The bright field image represents the morphology of cells in the tissue sample. The hematoxylin is a blue violet dye for staining basophilic tissues, such as cell nuclei, bone tissues, part of cartilaginous tissues, and serum components. The eosin is a red to pink color dye for staining acidophilic tissues, such as cytoplasms, connective tissues of soft tissues, erythrocytes, fibrin, and endocrine granules. FIG. 3 illustrates an exemplary bright field image of an HE-stained tissue sample.

Figure 4:
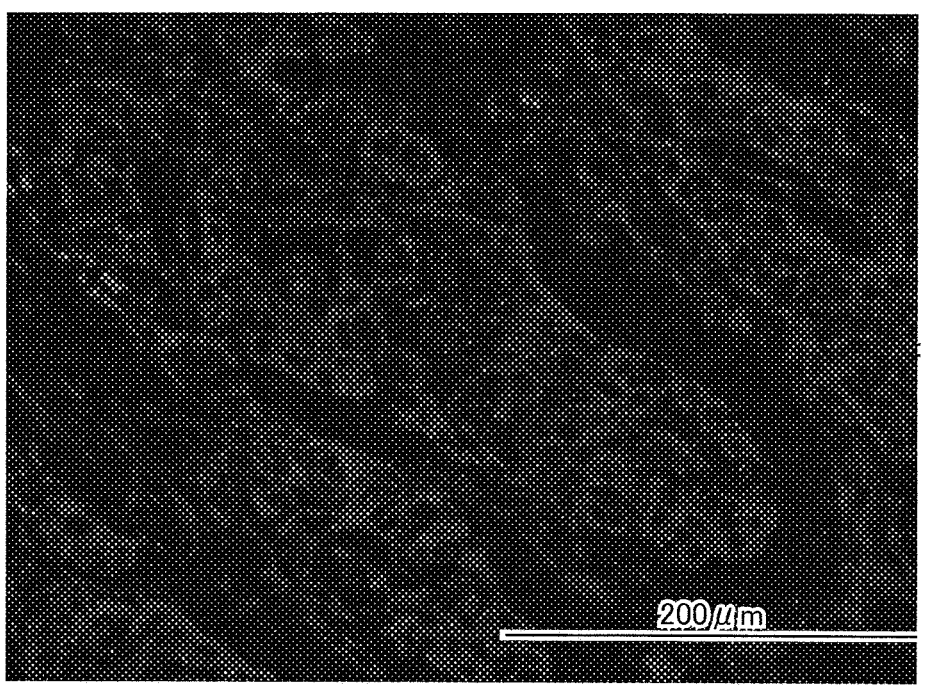
FIG. 4 is a diagram illustrating an exemplary fluorescent image.

The fluorescent image is a microscopic image obtained as follows: A tissue sample is stained with a staining reagent which contains a nanoparticle (a fluorescent particle) encapsulating a fluorescent substance which specifically labels a specific biological substance. The tissue sample is irradiated with an excitation light having a predetermined wavelength in the microscopic image acquiring device 1A so that the fluorescent particle emit light (fluorescent light). The fluorescent light is enlarged, focused, and photographed. In other words, the fluorescent light in the fluorescent image represents the expression of the specific biological substance in the tissue sample. FIG. 4 illustrates an exemplary fluorescent image.

<Acquisition of Fluorescent Image>

A method of acquiring the fluorescent image will now be described in detail, including the staining reagent used in acquisition of a fluorescent image and the method of staining a tissue sample with the staining reagent.

[Fluorescent Substance]

Examples of fluorescent substances used as the staining reagent for acquiring a fluorescent image include organic fluorescent dyes and quantum dots (semiconductor particles). The fluorescent substances preferably emit a visible light to a near-infrared light having a wavelength in the range of 400 to 1100 nm when excited by an ultraviolet light to a near-infrared light having a wavelength in the range of 200 to 700 nm.

Examples of the organic fluorescent dyes include fluorescein dye molecules, rhodamine dye molecules, Alexa Fluor (made by Invitrogen Corporation) dye molecules, BODIPY (made by Invitrogen Corporation) dye molecules, cascading dye molecules, coumarin dye molecules, eosin dye molecules, NBD dye molecules, pyrene dye molecules, Texas Red dye molecules, and cyanine dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (made by Invitrogen Corporation), methoxycoumarin, eosin, NBD, pyrene, Cy5, Cy5.5, and Cy7. These organic fluorescent dyes may be used alone or in combination.

The quantum dot may contain Group II-VI compounds, Group III-V compounds, or Group IV elements as a component (also referred to as a "Group II-VI quantum dot", "Group III-V quantum dot", or "Group IV quantum dot", respectively) can be used. These quantum dots may be used alone or in combination.

Specific examples thereof include, but should not be limited to, CdSe, CdS, CdTe, ZnSe, ZnS, ZnTe, InP, InN, InAs, InGaP, GaP, GaAs, Si, and Ge.

[Fluorescent Substance-Encapsulating Nanoparticle]

The fluorescent substance-encapsulating nanoparticle (fluorescent particle) in the present embodiment refers to a nanoparticle which have resin or silica as a base material and have a dispersed fluorescent substance inside or on the surface of the particle. The fluorescent substance and the nanoparticle may be chemically bonded or not.

The method of manufacturing a fluorescent particle encapsulating an organic phosphor (for example, a fluorescent organic dye, a quantum dot, etc.) includes forming a resin particle having a diameter in the order of nanometer and including an organic phosphor fixed inside or on the surface of a nanoparticle composed of resin or silica. The method of preparing the phosphor particle is not particularly limited and any known method can be used. For example, the organic phosphor is captured inside or on the surface of a (co)polymer by adding the organic phosphor during (co) polymerization of (co)monomer by an emulsion polymerization method to prepare a resin (a thermoplastic resin or a thermosetting resin) as the base material of the nanoparticle.

Preferred examples of the thermoplastic resin as the base material of the nanoparticle include a styrene resin, an acrylonitrile resin, a furan resin, and a resin similar to them. Preferred examples of the thermosetting resin as the base material of the nanoparticle include a xylene resin, polylactic acid, glycidyl methacrylate, a melamine resin, a urea resin, a benzoguanamine resin, a polyamide, a phenol resin, a polysaccharide, and a resin similar to them. Thermosetting resin, especially a melamine resin, is preferred in that it can prevent the dye encapsulated in the nanoparticle from being eluted even after dehydration with xylene, permeation, and sealing.

A polystyrene nanoparticle encapsulating an organic fluorescent dye can be prepared by a copolymerization process using an organic dye having a polymerizable functional group as described in U.S. Pat. No. 4,326,008 (1982), or by impregnation of a polystyrene nanoparticle with an organic fluorescent dye as described in U.S. Pat. No. 5,326,692 (1992).

A quantum dot having a core of a quantum dot and an outer shell may be used as a fluorescent particle. Throughout the specification, the quantum dot having a shell is represented, for example, as CdSe/ZnS where the core is CdSe and the shell is ZnS. Examples of usable quantum dots having a core of a quantum dot and a shell include, but should not be limited to, CdSe/ZnS, CdS/ZnS, InP/ZnS, InGaP/ZnS, Si/SiO2, Si/ZnS, Ge/GeO2, Ge/ZnS.

A quantum dot surface treated with an organic polymer may also be used when necessary. Examples of such quantum dots include CdSe/ZnS having surface carboxy groups (made by Invitrogen Corporation), and CdSe/ZnS having surface amino groups (made by Invitrogen Corporation).

A polymer nanoparticle encapsulating a quantum dot can be prepared by impregnation of a polystyrene nanoparticle with a quantum dot, as described in Nature Biotechnology vol. 19, p. 631 (2001).

The fluorescent particle used in the present embodiment may have any average particle size. When the particle size is too large, the quantitation result may be inaccurate because the binding of the particle to the biological substance is interfered. When the particle size is too small, quantitation may difficult because small amount of fluorescent substance included in one fluorescent particle and a luminance signal from such particle may be buried in background noise (e.g. noise of a camera and autofluorescence of cells). Accordingly, the fluorescent particle preferably has an average particle size in the range of 50 to 250 nm. The coefficient of variation (=(standard deviation/average value)×100%) showing the dispersion of the particle size is not particularly limited, but preferably 20% or less.

The average particle size of the fluorescent particle is calculated as follows. First, cross-sectional area of a fluorescent particle is measured in an electron microscopic photograph taken with a scanning electron microscope (SEM). The each measured area is regarded as the area of a circle, and the diameter of the circle is determined as the particle size. In the present application, the sizes of 1000 fluorescent particles are measured, and the arithmetic average is determined as the average particle size. The coefficient variation is also calculated based on the particle size distribution of 1000 particles.

[Surface Modification of Fluorescent Particles]

Surface modification is performed on a fluorescent particle so that the fluorescent particle can bind to or react with the target biological substance. The target biological substance may be any biological substance as long as there is a substance specifically bindable to the biological substance. Typical examples of the target biological substance include a protein (peptide), a nucleic acid (oligonucleotide and polynucleotide), and an antibody. Accordingly, examples of a substance specifically bindable to the target biological substance include an antibody which recognizes the target protein as an antigen, other protein specifically bindable to the target protein, and a nucleic acid having base sequences allowing hybridization to the target nucleic acid. Specific examples thereof include Ki67 antibody specifically bindable to Ki67 protein in a cell nucleus; anti-ER antibody specifically bindable to estrogen receptor (ER) in a cell nucleus; and anti-actin antibody specifically bindable to actin that forms a cell skeleton. Among these antibodies, anti-Ki67 antibody or anti-ER antibody is preferably bonded to fluorescent particles for selecting drugs for breast cancer.

The surface-modified fluorescent particle and the biological substance may bind to each other either directly or indirectly through other materials. For example, a fluorescent particle modified with streptavidin may be bind to a biological substance through a primary antibody specifically bindable to the biological substance and a secondary antibody which is biotinylated and specifically bindable to the primary antibody.

The primary antibody and the secondary antibody may be either polyclonal or monoclonal, and can be used in arbitrary combination, as long as the fluorescent particle can specifically bind to the specific biological substance.

Examples of the specific antigens are shown below. The antibodies recognizing the antigens are commercially available from a variety of antibody manufacturers, and can also be produced based on general knowledge. Examples of Gene Symbol are shown with corresponding Gene ID: APOE (ID:348), HMGA2 (ID:8091), HFN1A (ID:6927), ACE (ID:1636), ESR1 (ID:2099), HLA-B (ID:3106), LIPC (ID:3990), CYP19A1 (ID:1588), UGT1A1 (ID:54658), AR (ID:367), NFKB1 (ID:4790), PPARG (ID:5468), HMGA1 (ID:3159), VDR (ID:7421), THRB (ID:7068), ETV6 (ID:2120), APOA1 (ID335), NUP153 (ID:9972), RARB (ID:5915), NR3C1 (ID:2908), ESR2 (ID:2100), NCOA2 (ID:10499), LDLR (ID:3949), NUP98 (ID:4928), UGT1A9 (ID:54600), NKX2-1 (ID:7080), CETP (ID:1071), RELA (ID:5970), RGR (ID:5241), HLA-DRB1 (ID:3123), BMP2 (ID:650), PCNA (ID:5111), NFE2L2 (ID:4780), TP53 (ID:7157), IL10 (ID3586), IFNG (ID:3458), PPARA (ID:5465), ATXN3 (ID:4287), MDC1 (ID:9656), LCORL (ID:254251), NCOA3 (ID:8202), CRP (ID:1401), TOMM40 (ID:10452), CXCR4 (ID:7852), APOC3 (ID:345), NFKBIA (ID:4792), TNFSF11 (ID:8600), PCSK9 (ID:255738), CEBPB (ID:1051), HNF4A (ID:3172), ER, Ki67, p53, and PGR.

The fluorescent particle and the substance for surface modification of the fluorescent particle may be bonded in any form, for example, a covalent bond, an ionic bond, a hydrogen bond, a coordination bond, a physical adsorption, and a chemical adsorption. A strong binding, such as a covalent bond, is preferred from the viewpoint of stable binding.

An organic molecule may link between the substance for surface modification of the fluorescent particle and the fluorescent particle. For example, a poly(ethylene glycol) chain, such as SM(PEG)12 made by Thermo Scientific Inc., may be used to inhibit non-specific adsorption of a biological substance.

The fluorescent substance-encapsulating silica nanoparticle can be surface-modified by the same procedure as above, whether the fluorescent substance is composed of an organic fluorescent dye or composed of a quantum dot. For example, a silane coupling agent, which is widely used for binding inorganic substances to organic substances, can be used. The silane coupling agent has an alkoxysilyl group at one terminal of the molecule to yield a silanol group through hydrolysis, and a functional group (for example, a carboxyl group, an amino group, an epoxy group, or an aldehyde group) at the other terminal. The silane coupling agent is bound to an inorganic substance through an oxygen atom of the silanol group. Specific examples thereof include mercaptopropyltriethoxysilane, glycidoxypropyltriethoxysilane, aminopropyltriethoxysilane, and a silane coupling agent having a poly(ethylene glycol) chain (such as PEG-silane no. SIM6492.7 made by Gelest, Inc.). Two or more silane coupling agents may be used in combination.

The organic fluorescent dye-encapsulating nanoparticle may be reacted with a silane coupling agent according to a known procedure. For example, the organic fluorescent dye-encapsulating nanoparticle is dispersed in pure water, and aminopropyltriethoxysilane is added to be reacted with the nanoparticle at room temperature for 12 hours. After the reaction is completed, the product is centrifuged or filtered to yield organic fluorescent dye-encapsulating nanoparticle having a surface modified with an aminopropyl group. The amino group can be reacted with a carboxyl group in an antibody to bind the antibody with the organic fluorescent dye-encapsulating nanoparticle through an amido bond. A condensing agent, such as EDC (1-ethyl-3-[3-dimethylaminopropyl]carbodiimide hydrochloride: available from Pierce (registered trademark)), can also be used when necessary.

Optionally, a linker compound having a portion that can directly bind to an organic fluorescent dye-encapsulating nanoparticle modified with an organic molecule and another portion that can bind to a molecular target substance may be used. For example, sulfo-SMCC (sulfosuccinimidyl 4 [N-maleimidomethyl]-cyclohexane-1-carboxylate: available from Pierce) has both a site that can selectively react with an amino group and a site that can selectively react with a mercapto group. An organic fluorescent dye-encapsulating nanoparticle bonded to an antibody can be prepared using sulfo-SMCC, by connect the amino group of the organic fluorescent dye-encapsulating nanoparticle modified by aminopropyltriethoxysilane and a mercapto group of the antibody.

When a component for biological substance recognition is bound to each fluorescent substance-encapsulating polystyrene nanoparticle, the same procedure as above can be used whether the fluorescent substance is an organic fluorescent dye or a quantum dot. A fluorescent substance-encapsulating polystyrene nanoparticle having a functional group can be obtained by impregnating a polystyrene nanoparticle having a functional group, such as an amino group, with an organic fluorescent dye or a quantum dot. Subsequently, by using EDC or sulfo-SMCC, a fluorescent substance-encapsulating polystyrene nanoparticle having an antibody is provided.

[Staining Process]

The method of staining a tissue sample will now be described. The present invention can be applied not only to a tissue sample but also to a sample of cells fixed on a substrate and the like.

The method of preparing a sample applied to the staining process described below is not particularly limited. Samples prepared by any known method can be used.

1) Deparaffinizing Step

A tissue sample is immersed in xylene in a vessel to remove paraffin at any temperature, for example, at room temperature. A preferred immersion time is 3 minutes or more and 30 minutes or less. Xylene may be replaced with fresh one during the immersion as needed.

The tissue sample is then immersed in ethanol in a vessel to remove xylene. The immersion may be performed at any temperature, for example, at room temperature. A preferred immersion time is 3 minutes or more and 30 minutes or less. Ethanol may be replaced with fresh one during the immersion as needed.

The tissue sample is then immersed in water in a vessel to remove ethanol at any temperature, for example, at room temperature. A preferred immersion time is 3 minutes or more and 30 minutes or less. Water may be replaced with fresh one during the immersion as needed.

2) Retrieval Process

A target biological substance is retrieved by a known process. The retrieval may be performed under any condition, and may be performed with a solution for retrieval, such as a 0.01M citric acid buffer solution (pH: 6.0), a 1 mM EDTA solution (pH: 8.0), 5% urea, or a 0.1M trishydrochloric acid buffer solution. An autoclave, microwaves, a pressure pan, or a water bath may be used as a heater. The retrieval may be performed at any temperature, for example, at room temperature. The sample may be retrieved at a temperature of 50 to 130° C. for 5 to 30 minutes.

The activated sample is then immersed in phosphate buffered saline (PBS) in a vessel to wash the sample at any temperature, for example, at room temperature. A preferred immersion time is 3 minutes or more and 30 minutes or less. PBS may be replaced with fresh one during the immersion as needed.

3) Staining with a Surface-Modified Fluorescent Particle

A dispersion of a surface-modified fluorescent particle in PBS is placed on a tissue sample to react with a target biological substance. The surface modification is varied according to the biological substance to be stained. When several kinds of surface-modified fluorescent particles are used, the dispersion of each kind of fluorescent particles in PBS may be premixed or may be sequentially placed on the tissue sample.

The staining may be performed at any temperature, for example, at room temperature. A preferred reaction time is 30 minutes or more and 24 hours or less.

Prior to the staining with a fluorescent particle, a known blocking agent, such as BSA-containing PBS, is preferably added dropwise to the tissue sample.

Thereafter, the stained tissue sample is then immersed in PBS in a vessel to remove the unreacted fluorescent particle at any temperature, for example, at room temperature. A preferred immersion time is 3 minutes or more and 30 minutes or less. PBS may be replaced with fresh one during the immersion as needed. The tissue sample is covered with a cover glass to seal the tissue sample. A commercially available sealant may be used when necessary.

Staining with an HE staining reagent is performed before sealing the tissue sample with the cover glass.

In the above-described fluorescent staining method, the dispersion in PBS may be a mixed reagent, which is a mixture of a plural kinds of fluorescent particles surface-modified in the same way. The fluorescent particles in the mixture can be selected in any combination and in any number, as long as the fluorescence emitted by the encapsulated fluorescent substance of each particle can be separately photographed. Especially, it is preferred that the difference in excitation wavelength is as large as possible between the kinds of the fluorescent substances. The same applies to the difference in emission wavelength. Furthermore, it is preferred that the mixed fluorescent particles have the same configuration (for example, the structure of the surface modification, the material of the nanoparticle, average particle size, coefficient of variation of the particle size, and the like) except that the kind of the encapsulated fluorescent substance is different from each other, so that one molecule of the biological substance binds to only one fluorescent particle, that is, one molecule of the biological substance does not bind to two or more fluorescent particles.

[Acquisition of Fluorescent Image]

A wide-field microscopic image (a fluorescent image) of the stained tissue sample is taken with a microscopic image acquiring device 1A. In the microscopic image acquiring device 1A, an excitation light source and an optical filter for detecting fluorescent light are selected according to the maximum absorption wavelength and the emission wavelength of the fluorescent light of the fluorescent substance in the staining reagent.

<Operation of Pathological Diagnosis Support System 100 (Including Image Processing Method)>

The operation of the pathological diagnosis support system 100 to acquire and analyze the fluorescent image and the bright field image described above will now be described. Throughout the specification, the operation will be described in an exemplary case of observing a tissue sample stained with an HE staining reagent and a staining reagent containing a fluorescent particle bound to a component for biological substance recognition that can recognize a specific protein (hereinafter, referred to as a specific protein), but should not be limited to this.

First, an operator stains the tissue sample with two staining reagents, i.e., an HE staining reagent and a staining reagent containing a fluorescent labelling material including a fluorescent particle bound to the component for biological substance recognition that can recognize the specific protein.

After that, a bright field image and a fluorescent image of the tissue sample are obtained with the microscopic image acquiring device 1A according to the procedures (a1) to (a5):
(a1) The operator places the tissue sample stained with the HE staining reagent and the staining reagent containing the fluorescent particle on a microscopic slide, and sets the slide on the slide fixation stage of the microscopic image acquiring device 1A;
(a2) The operator sets a bright field unit, and adjusts the magnification for photographing and the focus so that the target region of the tissue sample is in the field;
(a3) The operator photographs the tissue sample with the photographing unit to generate image data of the bright field image, and transmits the image data to the image processing device 2A;
(a4) The operator replaces the bright field unit with a fluorescence unit; and
(a5) The operator selects an emission light and a filter suitable for exciting the fluorescent particles in the staining reagent, photographs the tissue sample with the photographing unit without changing the field and the magnification to generate image data of the fluorescent image of fluorescence emitted from the staining reagent, and transmits the image data to the image processing device 2A.

When a mixed reagent is used for the fluorescent staining, for example, including two surface-modified fluorescent particles (hereinafter referred to as staining reagent (A) and staining reagent (B)), the following step is executed after the step of (a4) for acquiring fluorescent images:
(a5) The operator selects an emission light and a filter suitable for exciting the fluorescent particle in the staining reagent (A), photographs the tissue sample with the photographing unit without changing the field and the magnification to generate image data of the fluorescent image of fluorescence emitted from the staining reagent (A), and transmits the image data to the image processing device 2A.
(a6) The operator selects an emission light and a filter suitable for exciting the fluorescent particle in the staining reagent (B), photographs the tissue sample with the photographing unit without changing the field and the magnification to generate image data of the fluorescent image of fluorescence emitted from the staining reagent (B), and transmits the image data to the image processing device 2A.

In the image processing device 2A, image analysis of the bright field image and the fluorescent image are performed.

Figure 5:
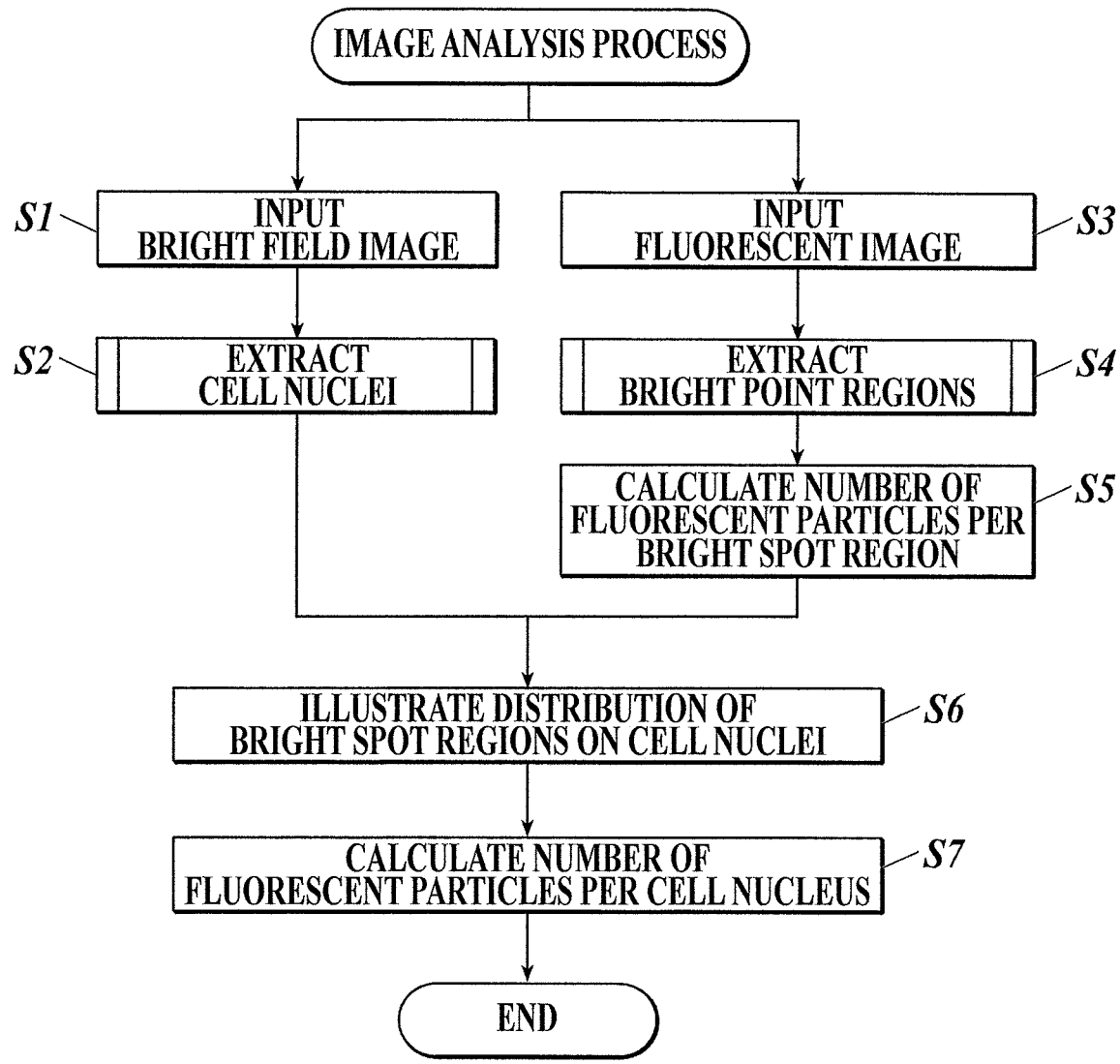
FIG. 5 is a flowchart illustrating image analysis executed by the controller in FIG. 2.

FIG. 5 illustrates a flowchart of the image analysis in the image processing device 2A. The image analysis illustrated in FIG. 5 is executed in cooperation with the controller 21 and the program stored in the storage 25.

When the bright field image transmitted from the microscopic image acquiring device 1A is input into the communication interface 24 (Step S1), regions of cell nuclei are extracted from the bright field image (Step S2).

Figure 6:
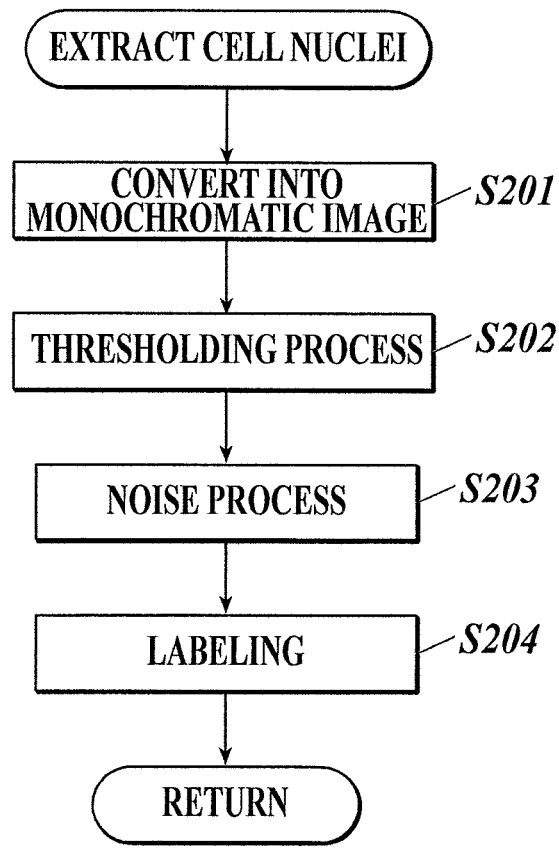
FIG. 6 is a flowchart illustrating detailed process in Step S2 of FIG. 5.

FIG. 6 illustrates the detailed flow of the process in Step S2. The process in Step S2 is executed in cooperation with the controller 21 and the program stored in the storage 25.

In Step S2, the bright field image is converted into a monochromatic image (Step S201). FIG. 7A illustrates an exemplary bright field image.

A binary image is then prepared by binarizing the each pixel value in the monochromatic image by thresholding process by using a predetermined threshold value (Step S202).

In the next step, noise reduction process is performed (Step S203). The noise reduction can be performed, for example, by subjecting the binary image to a closing process. The closing process includes dilation process followed by erosion process executed as many times as the dilation process. In the dilation process, a target pixel is replaced with a white pixel if at least one white pixel is present within the range of n×n pixels from the target pixel (where n is an integer of 2 or more). In the erosion, the target pixel is replaced with a black pixel if at least one black pixel is present within the range of n×n pixels from the target pixel. The closing process can remove small regions such as noise. FIG. 7B illustrates an exemplary image after the noise reduction process. An image of extracted cell nuclei (cell nucleus image) is obtained after the noise reduction process as in FIG. 7B.

In the next step, the image after the noise reduction process is subjected to labelling process to assign label to each of the extracted cell nuclei (Step S204). In the labelling process, the same label (number) is assigned to contiguous pixels in an image and for identification of an object. By the labelling process, the cell nuclei in the image after noise reduction can be identified and labelled.

Meanwhile, if the fluorescent image transmitted from the microscopic image acquiring device 1A is input into the communication interface 24 (Step S3: input step), bright spot regions are extracted from the fluorescent image (Step S4).

FIG. 8 illustrates the detailed flow of the process in Step S4. The process in Step S4 is executed in cooperation with the controller 21 and the program stored in the storage 25.

Figure 9A:
FIG. 9A is a diagram illustrating a fluorescent image.

In Step S4, first, color components are extracted from the fluorescent image according to the wavelengths of the fluorescent bright spots (Step S401). In Step S401, if the emission wavelength of the fluorescent particle is 615 nm, for example, only the fluorescent bright spots having the wavelength component are extracted as an image. FIG. 9A illustrates an exemplary fluorescent image.

Figure 9B:
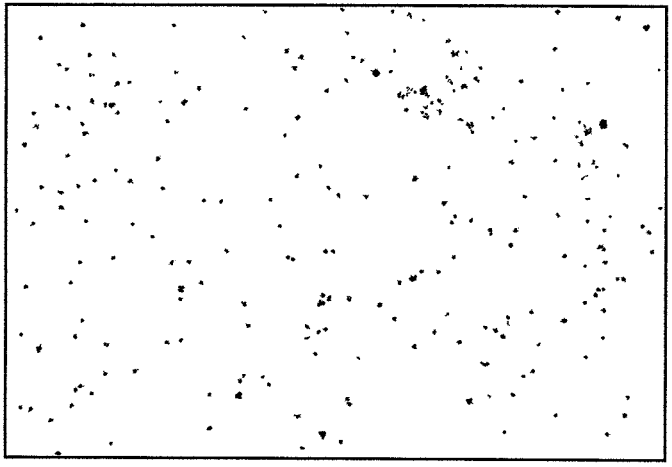
FIG. 9B is a diagram illustrating an image of bright spot regions.

In the next step, the extracted image is subjected to a thresholding process to generate a binary image and to extract bright spot regions (Step S402). FIG. 9B illustrates an exemplary image of extracted bright spot regions centering around a fluorescent bright spot.

Noise removal process for removing autofluorescence of cells or other unnecessary signal components may be executed prior to the thresholding process in step S402. A low-pass filter, such as a Gaussian filter, or a high-pass filter, based on a second derivative, is preferably used.

Subsequently, labelling process is executed to label each of the extracted bright spot regions (Step S403).

After the process in Step S4 is completed, the process returns to the steps in FIG. 5 to calculate the number of the fluorescent particles in each bright spot region (Step S5). The information of the calculated number of fluorescent particles in each bright spot region is added to the label of the bright spot region assigned in Step S404.

After the processes in Step S2 and Step S5 are completed, the cell nucleus image (FIG. 7B) and the bright spot region image (FIG. 9B) are superimposed by a superimposing process. The distribution of the bright spot regions in the cell nuclei is shown on the display 23 of the image processing device 2A (step S6), and the number of fluorescent particles per cell nucleus is calculated (step S7: quantitation step).

According to the above-described present embodiment, cell nuclei are extracted through the processes in Steps S1 and S2. The number of fluorescent particles in each bright spot region is calculated through Steps S3 to S5. Through the process of Step S6, the distribution of the bright spot regions on the cell nuclei is actually shown and the number of fluorescent particles per cell nucleus is calculated.

When the mixed reagent is used for fluorescent staining and a plurality of fluorescent images are acquired by the microscopic image acquiring device 1A, the number of fluorescent particles per cell nucleus is calculated from each of the fluorescent images by the processes in steps S3 to S7. After the process of step S7 is executed for all the fluorescent images, the numbers of the fluorescent bright spots calculated from the fluorescent images are summed for each cell nucleus (summing step) to calculate the total number of the fluorescent bright spots per cell nucleus.

The above-descried embodiment is a suitable example of the present invention, and the present invention should not be limited to this.

The embodiment of the present invention includes a kit for performing quantitation of nucleoprotein in the above embodiment. The kit includes fluorescent particles used in the above embodiment as a component. Furthermore, the kit preferably includes the primary antibody and the secondary antibody selected according to the kind of the nucleoprotein of the quantitation target. More preferably, the kit includes a staining reagent for extracting the morphology of cells (for example, HE staining reagent), liquid for dilution in staining, sealant, and a manual describing the quantitation method.

While only one kind of specific protein is the quantitation target in the above-described embodiment, a plurality of specific proteins may be targeted by using two or more fluorescent particles having a emission wavelength different from each other.

In such a case, fluorescent images are obtained for each emission wavelength of the fluorescent particle as described above, and the process of steps S3 to S7 is executed for each of the fluorescent images. Otherwise, for example, each of the color components is extracted using filters in Step S401, the process in Steps S402 to S5 is executed for each of the extracted color components (wavelength components), and a cell image and fluorescent particle images for each of the color components are superimposed in Step S6 to calculate the number of each of the fluorescent particles.

In the above embodiment, the exemplary mixed reagent is a dispersion in PBS including a mixture of two kinds of fluorescent particles surface-modified in the same way, however, the dispersion may include a mixture of three or more kinds of fluorescent particles.

If the number of colors is increased in the mixed fluorescent particles, the probability that the adjacent specific protein is stained with different fluorescent particles increases. Accordingly, accurate quantitation is possible because of the increased probability that the densely distributed fluorescent substances are calculated separately.

The description above discloses an example in which an HDD or a semiconductor nonvolatile memory is used as a computer-readable medium for the program according to the present invention, but the present invention should not be limited to this. Another computer-readable medium may also be used, for example, a portable recording medium, such as CD-ROM. Carrier waves can also be used as a medium that provides data of the program according to the present invention through a communication line.

The detailed configurations and operations of the devices forming the pathological diagnosis support system 100 can also be appropriately modified within the scope of the present invention.

EXAMPLES (A) Preparation of Fluorescent Substance-Encapsulating Melamine Nanoparticles 2.5 mg of Alexa Fluor 488 (made by Life Technologies Corporation) as a fluorescent substance was dissolved in 22.5 mL of water. The solution was heated at 70° C. on a hot stirrer for 20 minutes, and 1.5 g of a melamine resin raw material NIKALAC MX-035 (made by NIPPON CARBIDE INDUSTRIES CO., INC., weight-average polymerization degree: 1.5) was added to the solution. The solution was further heated with stirring for 5 minutes. After addition of 100 µl of formic acid and heating at 60° C. for 20 minutes with stirring, the solution was allowed to cool at a room temperature. After cooling, the reaction mixture was put into a tube for centrifugation and centrifuged at 12000 rpm for 20 minutes. After removal of supernatant, the obtained particle is re-dispersed into 1 ml of pure water to obtain a butylated hydroxytoluene dye-encapsulating melamine resin nanoparticle as a fluorescent substance-encapsulating melamine nanoparticle.

Observation of the obtained Alexa Fluor 488-encapsulating nanoparticle with a scanning electron microscope (SEM; S-800 made by Hitachi, Ltd.) revealed that the average particle size was 150 nm.

(B) Surface Modification of Fluorescent Particle 0.1 mg of the fluorescent substance-encapsulating melamine nanoparticle obtained in the above (A) were dispersed in 1.5 ml of ethanol. 2 µL of aminopropyltrimethoxysilane (LS-3150, made by Shin-Etsu Chemical Co., Ltd.) was added to perform surface amination reaction for eight hours.

Subsequently, the concentration was adjusted to 3 nM by adding 2 mM of EDTA (ethylenediaminetetraacetic acid) in PBS (phosphate buffered saline). SM(PEG)12 (succinimidyl-[(N-maleomidopropionamid)-dodecaethyleneglycol]

ester, made by Thermo Scientific, Inc.) was added to the solution such that the final concentration was 10 mM. After reaction for 1 hour, the mixture was centrifuged at 10000 G for 20 minutes and the supernatant was removed. 2 mM of EDTA in PBS was added to disperse the precipitate and to centrifuge again. The washing operation was performed three times as above to prepare a fluorescent substance-encapsulating melamine nanoparticle having maleimido groups at terminals.

Meanwhile, thiol groups were added to streptavidin (made by Wako Pure Chemical Industries, Ltd.) using N-succinimidyl S-acetylthioacetate (SATA). By subsequent filtration through a gel filtration column, a solution of streptavidin bindable to the fluorescent substance-encapsulating melamine nanoparticle was prepared.

The above-described fluorescent substance-encapsulating melamine nanoparticles and the streptavidin were mixed in 2 mM of EDTA in PBS and reacted for one hour. 10 mM of Mercaptoethanol was added to terminate the reaction. The obtained solution was condensed with a centrifugal filter, and was passed through a gel filtration column for purification to remove unreacted streptavidin and other impurities. Fluorescent substance-encapsulating melamine nanoparticle binding to streptavidin was thereby prepared. The prepared fluorescent SUBSTANCE-encapsulating melamine nanoparticle binding to streptavidin were stored at 4° C. and, right before usage for tissue staining, sonicated and diluted with a blocking solution (made by Dako, Antibody Diluent with Background Reducing Components, S3022) such that the final concentration of the nanoparticle was adjusted to 0.2 nM in the staining reagent.

(c) Staining of Tissues

Adjacent slices of the same specimen from the formalin-fixed and paraffin-embedded tissue array of human breast tissue (made by US Biomax, Inc., Product name: paraffin-embedded breast cancer tissue array, Product number: BR243) was stained by the following procedure.

First, the tissue sample was subjected to deparaffinizing treatment using xylene and hydrophilic treatment for removing the xylene. Subsequently, the tissue sample was put into citric acid buffer solution (pH 6.0) and heated (120° C. for 5 minutes) for retrieval.

Subsequently, the tissue sample was subjected to washing with PBS, blocked by reaction with the above-described blocking solution for 15 minutes at room temperature, and reacted with primary antibody and secondary antibody described in TABLEs 1 and 2.

Specifically, for example, a primary antibody MIB-1 (made by Dako), which is a mouse monoclonal antibody directed against Ki67 protein as an antigen, was diluted with the above blocking solution to have a concentration of 0.61 µg/ml, placed on the tissue sample after blocking, and left at 4° C. overnight. The tissue sample was washed with PBS. A secondary antibody of biotinylated LO-MG1-13 (made by AbD Ltd., No. MCA1289), which is a monoclonal anti-mouse antibody, was diluted to have a concentration of 2 µg/ml with the above blocking solution and was placed on the tissue sample and left at room temperature for 30 minutes. The biotinylation of the secondary antibody was performed by known method with Biotin Labeling Kit-SH (made by DOJINDO LABORATORIES, product code: LK10).

The staining reagent prepared in above (B) was placed on the tissue sample reacted with the primary antibody and the secondary antibody and was left for 30 minutes to 1 hour at room temperature. After washing, the tissue sample was reacted by 4% paraformaldehyde for 10 minutes at room temperature in order to fix the fluorescent particle to the tissue sample. Fluorescent staining was thereby performed.

Subsequently, the cell nuclei are stained with a commercially available HE staining reagent and sealed with Entellan® new (made by Merck Ltd.).

Tissue samples are also reacted with each of the combinations of the primary antibody and the secondary antibody described in TABLES 1 and 2, using commercially available reagents by well-known methods. Ki67 protein is the specific protein subjected to fluorescent staining by the combination of the primary antibody (anti-Ki67 antibody) and the secondary antibody described in TABLE 1. ER protein is the specific protein subjected to fluorescent staining as the specific protein by the combination of the primary antibody (anti-ER antibody) and the secondary antibody described in TABLE 2.

The name of each antibody described in TABLES 1 and 2 is a clone name of a monoclonal antibody or a product code of a polyclonal antibody. The name of animals (host) used to prepare the primary antibody is described in parenthesis under the clone name of primary antibody. SP6, EPR3610, B126.1, 4A1, 5D7, RG-16, SB115h, SB77e, 6F11, 14C8, 1D5, Ab15580, Ab97109, Ab97042, Ab97052, Ab97047, Ab97106, and Ab30656 are made by Abcam, LO-MG7 is made by Acris Antibodies, Inc., LO-RG1 and LO-MG2a-7 are made by AbD Serotec, Sc-7877 is made by Santa Cruz Biotechnology, Inc., and LS-C178370 is made by LifeSpan Biosciences, Inc.

The tissue section adjacent to the tissue section stained by the fluorescent particle was stained with the conventionally known DAB for comparing with the result of staining according to the present invention using the fluorescent particle.

(D) Image Analysis

Microscopic images (bright field image and fluorescent image) of the stained tissue sample were acquired with super resolution microscopy made by Nikon, N-SIM. The fluorescent image was acquired under an excitation light having a wavelength of 490 nm by capturing the fluorescence having a wavelength of about 540 nm (a central wavelength).

Regions of cell nuclei were extracted from the acquired bright field image on the basis of the hematoxylin staining.

The number of bright spots was counted from the acquired fluorescent image by the method described in Japanese Patent Application Laid-Open Publication No. 2013-57631. Specifically, a binary image was prepared from the obtained fluorescent image based on a predetermined higher threshold and a lower threshold. The higher threshold and the lower threshold may be determined by statistical threshold determination, such as binarization according to Otsu's discrimination analysis (Nobuyuki Otsu; Hanbetsu oyobi Saishojijokijunni motoduku Jidosikiichi senteiho (Method of Automatically Selecting Thresholds Based on Discrimination and Least Square Criterion), Journal of The Institute of Electronics, Information and Communication Engineers, Vol. J63-D, No. 4, pp. 349-356, 1980), for example. The number of bright spots in the binary image was counted with bright spot measuring software "G-count" made by G-Angstrom K.K.

Subsequently, the bright field image and the fluorescent image were superimposed. The bright spots in and outside of the cell nuclei in the superimposed image were calculated.

(E) Experimental Result

The results by the fluorescent staining with the fluorescent particles of the present invention and the results by DAB method are compared using the same primary antibody and secondary antibody combined. The evaluation according to the present invention was equivalent to that by the DAB method, regarding the expression ratio (the ratio of cells expressing the specific protein among all the cells) of specific protein (Ki67 protein or ER protein).

Furthermore, the expression amount of the specific protein per cell nucleus region was quantitatively evaluated. Because the quantitation results by the DAB method varied largely even when the expression ratios of the specific protein in samples were almost the same, stable quantitative evaluation was not possible. Meanwhile, by the method of the present invention with a fluorescent particle, the difference in quantitation results depended on the expression ratio of the specific protein. Furthermore, the present invention provides small error and a good reproducibility in quantitative evaluation even when the measuring person or system for measurement was different, because the expression amount can be calculated as the number of fluorescent bright points.

Hereinafter, more detailed evaluation is described regarding accuracy of quantitating specific protein according to the present invention.

TABLEs 1 and 2 show evaluation results based on the number of bright spots outside of cell nuclei per image of a sample in which Ki67 protein and ER protein are respectively subjected to fluorescent staining by the method according to the present invention. The symbol "⊚ (double circle)" means 9 or less bright spots outside of the cell nuclei, "○ (circle)" means 10 to 99 bright spots, and "Δ (triangle)" means 100 to 200 bright spots. The symbol "—" means that evaluation is not performed.

Because Ki67 protein and ER protein are expressed in cell nuclei, bright spots outside of cell nuclei do not mean the expression of Ki67 protein or ER protein, but mean noise due to nonspecific staining. The less noise (i.e. fewer bright spots outside of cell nuclei) suggests less noise in the bright spots in a cell nuclei and high accuracy in quantitation.

As shown in TABLE 1, Ki67 protein in samples can be automatically quantitated by staining Ki67 protein with a staining reagent including the fluorescent particle. Because adjacent slices of the same specimen are used as tissue samples, the number of bright spots in cell nuclei is considered to be almost the same by using any of the combinations of primary antibody and secondary antibody. The number of bright spots in cell nuclei practically measured from each image was almost the same, i.e. approximately 2500. Therefore, according to the present invention, stable quantitative result can be obtained regardless of the combination of antibodies.

When either the primary antibody or the secondary antibody was monoclonal antibody, there was often less noise (i.e. fewer bright spots outside of cell nuclei, evaluated to be "○ (circle)" or "⊚ (double circle)") compared to when both the primary antibody and the secondary antibody were polyclonal antibodies. This suggests that the bright spots in cell nuclei also include less noise and that highly accurate quantitation is possible. Furthermore, when both the primary antibody and the secondary antibody were monoclonal antibodies, the number of bright spots outside of cell nuclei was less than 9 (evaluated to be "⊚ (double circle)") and the number of bright spots in cell nuclei was approximately 2500 for all the combinations of primary antibody and the secondary antibody. In view of the above, the quantitation accuracy according to the present invention is considered to be extremely high.

TABLE 2

| | | PRIMARY ANTIBODY | | | |
| | | MONOCLONAL | | | POLYCLONAL |
| SECONDARY ANTIBODY | | 6FI1 (mouse) | 14C8 (mouse) | ID5 (rabbit) | Ab30656 (rabbit) |
|---|---|---|---|---|---|
| MONO-CLONAL | LO-MG7 | ○ | ⊚ | — | — |
| | LO-MG1-13 | ⊚ | — | — | — |
| | LO-RG1 | — | — | ○ | ○ |
| POLY-CLONAL | Ab97042 | ○ | Δ | — | — |
| | Ab97047 | — | — | ○ | Δ |

As shown in TABLE 2, ER protein in samples can be automatically quantitated by staining ER protein with a staining reagent including the fluorescent particles. Because the tissue samples are adjacent slices of the same specimen, the numbers of bright spots in cell nuclei are considered to be almost the same in any of the combinations of primary antibody and secondary antibody. The practically measured numbers of bright spots in cell nuclei per image were almost the same, i.e. approximately 1200. Therefore, according to the present invention, stable quantitative result can be obtained regardless of the combination of antibodies.

When either the primary antibody or the secondary antibody is monoclonal antibody, there is often less noise (i.e. number of bright spots outside of cell nuclei are less than 99, evaluated to be ○ (circle)) compared to when both the

TABLE 1

| | | PRIMARY ANTIBODY | | | | | | | | |
| | | MONOCLONAL | | | | | | POLYCLONAL | | |
| SECONDARY ANTIBODY | | SP6 (rabbit) | EPR3610 (rabbit) | B126.1 (mouse) | 4A1 (mouse) | MIB-1 (mouse) | 5D7 (rat) | Ab15580 (rabbit) | Sc-7877 (goat) | LS-C178370 (mouse) |
|---|---|---|---|---|---|---|---|---|---|---|
| MONOCLONAL | LO-RG1 | ⊚ | ⊚ | — | — | — | ⊚ | ○ | — | — |
| | RG-16 | ⊚ | ⊚ | — | — | — | — | Δ | — | — |
| | LO-MG1-13 | — | — | ⊚ | ⊚ | ⊚ | — | — | — | ○ |
| | LO-MG2a-7 | — | — | ⊚ | ⊚ | — | — | — | — | ○ |
| | SB115h | — | — | — | — | — | — | — | ○ | — |
| | SB77e | — | — | — | — | ⊚ | — | — | — | Δ |
| POLYCLONAL | Ab97109 | — | — | ○ | ○ | — | — | — | — | Δ |
| | Ab97042 | — | — | ○ | ○ | — | — | — | — | ○ |
| | Ab97052 | — | — | — | — | — | ○ | — | — | — |
| | Ab97047 | ○ | ⊚ | — | — | — | — | Δ | — | — |
| | Ab97106 | — | — | — | — | — | — | — | Δ | — | primary antibody and the secondary antibody are polyclonal antibodies. Accordingly, it is suggested that the bright spots in cell nuclei also include less noise and that highly accurate quantitation is achieved. Furthermore, considering that the number of bright spots outside of cell nuclei is less than 99 (evaluated to be ○ (circle) or ⊚ (double circle)) for all the four examples in which primary antibody and the secondary antibody are both monoclonal antibodies, and that the number of bright spots in cell nuclei are approximately 1200 for two of the four examples, the quantitation accuracy according to the present invention is considered to be extremely high.

A polyclonal antibody includes a mixture of several kinds of antibody components and generally reacts with a plurality of epitopes on the antigen in immunostaining. As a result, the staining efficiency is high and the expression of the specific protein can be detected with high sensitivity. Meanwhile, a monoclonal antibody is composed of one kind of antibody component and reacts with only one epitope on an antigen. As a result, highly specific staining with less noise is performed; however, quantitation is difficult with conventional fluorescent dye or enzyme because the luminance of bright spots very low or the coloring by enzyme reaction is very weak. According to the quantitation method of the present invention, the luminance per particle is high enough so that highly sensitive detection and easy quantitation of a biological substance can be achieved even when a monoclonal antibody is used. Furthermore, according to the quantitation method of the present invention, a monoclonal antibody is more preferable than a polyclonal antibody because the fluorescent bright points outside of cell nuclei using a monoclonal antibody are less than those using a polyclonal antibody, that is, the quantitation result includes less noise and is more accurate.

Modified Example

Fluorescent substance-encapsulating melamine nanoparticles modified with streptavidin and encapsulating Alexa 647 (made by Life Technologies Corporation) were prepared by the same procedures as (A) to (B) in the EXAMPLES, except that Alexa 647 was used instead of Alexa 488. A staining reagent including the nanoparticle with a concentration of 0.2 nM of was prepared. By adding an equivalent amount of the staining reagent including Alexa 488 prepared in the EXAMPLES, a mixed reagent including two kinds of fluorescent particles with a total concentration of 2 nM was prepared.

Subsequently, tissue staining was performed in the same way as the staining step (C) in the EXAMPLES, except that the mixed reagent was used as the staining reagent.

Subsequently, a fluorescent image was acquired under an excitation light having a wavelength of 490 nm by capturing the fluorescence having a wavelength of about 540 nm (a central wavelength), and another fluorescent image was acquired under an excitation light having a wavelength of 650 nm by capturing the fluorescence having a wavelength of about 665 nm (a central wavelength). The fluorescent images were respectively subjected to image analysis as in (D) in order to calculate the number of bright spots in cell nuclei and the number of bright spots outside of cell nuclei in the images. The total number of bright spots in cell nuclei and the total number of bright spots outside of cell nuclei were further calculated by summing the numbers of bright spots in cell nuclei and numbers of bright spots outside of cell nuclei calculate from the images.

(Result of Experiment)

The obtained results were equivalent to those in the EXAMPLES, regarding the evaluation of expression ratio of specific protein compared with DAB method as in EXAMPLES and the evaluation of quantitative accuracy on the basis of the numbers of bright spots outside of cell nuclei per image.

In all the samples, the number of bright spots in cell nuclei per image was almost the same and about 10000. Thus, more bright points were measured by using two kinds of fluorescent particles having different fluorescent wavelengths than in the EXAMPLES. The reason is considered as follows:

When the fluorescent particles used for staining have small average size and the biological substance of the staining target is expressed densely as Ki67 protein or ER protein, the fluorescent particles are likely to be disposed with an interval smaller than the resolution of the microscope. When the number of colors of the fluorescent particles used for fluorescent staining is one, fluorescent particles disposed in proximity to each other cannot be measured separately but are observed as one bright point. Accordingly, the number of bright spots is limited depending on the resolution of the microscope.

According to the MODIFIED EXAMPLES using two kinds of fluorescent particles having different fluorescent wavelengths for staining, fluorescent particles can be measured separately even when they are disposed in proximity to each other with an interval smaller than the resolution of the microscope, provided that the fluorescent wavelengths of them are different from each other. As a result, it is considered that accuracy in measuring the number of bright spots was improved.

That is, according to the quantitation method using a mixed reagent as in the MODIFIED EXAMPLES, highly accurate quantitation is possible even when fluorescent particles for staining have an average size smaller than the above-described limit determined by the resolution of the microscope (about 100 nm in the case of super resolution microscopy).

As described above, according to the biological substance quantitation method of the present invention, the expression amount of a specific protein can be quantitated with high accuracy on the basis of the number of bright spots from the fluorescent particles.

Furthermore, when at least one of, preferably both of, the primary antibody and the secondary antibody are monoclonal antibody, nonspecific bright spots which do not represent the specific protein are reduced and the quantitation result is highly reliable.

Any biological substance other than the Ki67 protein or ER protein can be quantitated by the method according to the present invention. Moreover, by altering the component for biological substance recognition used to take fluorescent images according to the type of the pathological change (cancer) of diagnostic objects, medical doctors can be provided with a feature amount which quantitatively indicates the expression level of a biological substance.

INDUSTRIAL APPLICABILITY

The present invention can be preferably applied in image analysis of images used for pathological diagnosis.

DESCRIPTION OF REFERENCE NUMERALS 1A microscopic image acquiring device
2A image processing device
3A cable 21 controller
22 operation unit
23 display
24 communication interface
25 storage
26 bus
100 pathological diagnosis supporting system

The invention claimed is:

1. A pathological diagnosis support system of quantitating a target substance in a sample stained with a staining reagent comprising a fluorescent particle encapsulating a fluorescent substance, based on a fluorescence of the fluorescent substance, the system comprising:
a sample containing a target substance that has been stained with a staining reagent comprising a fluorescent particle encapsulating a fluorescent substance;
an input unit comprising a microscopic image acquiring device, to which a fluorescent image of a fluorescent bright spot representing the target substance in the stained sample is input, the fluorescent bright spot comprising a fluorescence emitted by the fluorescent particle encapsulating the fluorescent substance, and the sample comprising the fluorescent particle bound to the target substance; and
an image processing device that quantitates an expression amount of the target substance based on the fluorescence of the fluorescent bright spot,
wherein
the target substance is a nucleoprotein expressed at a cell nucleus,
the fluorescent particle binds to the target substance through a primary antibody which is directed against the target substance as an antigen, and
the primary antibody is a monoclonal antibody.

2. The pathological diagnosis support system according to claim 1, wherein
the fluorescent particle binds to the target substance through a secondary antibody which is directed against the primary antibody as an antigen, and
the secondary antibody is a monoclonal antibody.

3. The pathological diagnosis support system according to claim 1, wherein the nucleoprotein is Ki67 protein.

* * * * *